United States Patent
Tajima

(10) Patent No.: US 8,562,920 B2
(45) Date of Patent: Oct. 22, 2013

(54) MICRO PLATE TREATING DEVICE AND MICRO PLATE TREATING METHOD

(75) Inventor: Hideji Tajima, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 964 days.

(21) Appl. No.: 12/225,747

(22) PCT Filed: Mar. 28, 2007

(86) PCT No.: PCT/JP2007/056599
§ 371 (c)(1),
(2), (4) Date: Sep. 3, 2009

(87) PCT Pub. No.: WO2007/111347
PCT Pub. Date: Oct. 4, 2007

(65) Prior Publication Data
US 2010/0047132 A1    Feb. 25, 2010

(30) Foreign Application Priority Data
Mar. 28, 2006  (JP) .................................. 2006-089286

(51) Int. Cl.
  B01L 3/02    (2006.01)
  B03C 1/30    (2006.01)
  C02F 1/48    (2006.01)
  G01N 33/553  (2006.01)

(52) U.S. Cl.
  USPC .......................... 422/552; 210/222; 436/526

(58) Field of Classification Search
  USPC ........................ 422/501, 521, 552, 553, 522
  See application file for complete search history.

(56) References Cited

U.S. PATENT DOCUMENTS

| | | |
|---|---|---|
| 5,702,950 A | 12/1997 | Tajima |
| 5,895,631 A | 4/1999 | Tajima |

(Continued)

FOREIGN PATENT DOCUMENTS

| | | |
|---|---|---|
| EP | 687501 | 12/1995 |
| EP | 763739 | 3/1997 |

(Continued)

OTHER PUBLICATIONS

International Search Report issued May 29, 2007 by the ISA/JP, in connection with International Application No. PCT/JP2007/056599.

(Continued)

Primary Examiner — Jill Warden
Assistant Examiner — Brittany Fisher
(74) Attorney, Agent, or Firm — Haynes and Boone, LLP

(57) ABSTRACT

An object is to provide a micro plate treating device and micro plate treating method capable of handling a larger number of kinds of solution or suspensions or a larger volume of solutions or suspensions per work area by use of a normalized micro plate without enlarging the scale of the device.

The micro plate treating device comprises a micro plate having wells arranged in a matrix form, one or two or more nozzle heads each having nozzles capable of sucking and discharging a fluid and arranged in a matrix form, and moving means capable of moving relatively an interval between the micro plate and the nozzle heads, wherein tips of all the nozzles are configured to be permitted to be simultaneously inserted into some of the wells in the micro plate, at least one of the row interval or the column interval of the nozzles is set to a natural number multiple of the row interval or the column interval of the corresponding wells, the natural number being two or more, and at least one of the row number or the column number of all the corresponding nozzles is one to the natural number of the row number or the column number of the wells.

9 Claims, 9 Drawing Sheets

(56) References Cited

U.S. PATENT DOCUMENTS

| | | | |
|---|---|---|---|
| 6,485,690 B1 * | 11/2002 | Pfost et al. | 422/552 |
| 6,509,193 B1 * | 1/2003 | Tajima | 436/49 |
| 6,805,840 B1 * | 10/2004 | Tajima | 422/501 |
| 6,998,055 B2 * | 2/2006 | Tajima | 210/695 |
| 7,267,800 B2 * | 9/2007 | Takii et al. | 422/501 |
| 7,384,559 B2 * | 6/2008 | a Brassard | 210/695 |
| 2003/0075556 A1 | 4/2003 | Tajima et al. | |
| 2004/0022689 A1 * | 2/2004 | Wulf et al. | 422/100 |

FOREIGN PATENT DOCUMENTS

| | | |
|---|---|---|
| EP | 1243929 | 9/2002 |
| JP | 8062224 | 3/1996 |
| JP | 8-320274 | 12/1996 |
| JP | 11-271193 | 10/1999 |
| JP | 3115501 | 9/2000 |
| JP | 2001-13152 | 1/2001 |
| JP | 2001-183382 | 7/2001 |
| JP | 2005-77308 | 3/2005 |
| JP | 2006-78356 | 3/2006 |
| WO | WO/99/47267 | 9/1999 |
| WO | WO 01/48487 | 7/2001 |

OTHER PUBLICATIONS

Written Opinion issued May 29, 2007 by the ISA/JP, in connection with International Application No. PCT/JP2007/056599.
International Preliminary Report on Patentability issued Aug. 5, 2008 by the IPEA/JP, in connection with International Application No. PCT/JP2007/056599.

* cited by examiner

MICRO PLATE TREATING DEVICE AND MICRO PLATE TREATING METHOD

CROSS REFERENCE

This application is a United States national phase application of co-pending international patent application number PCT/JP2007/056599, filed Mar. 28, 2007,which claims priority to Japanese patent application number 2006-089286, filed Mar. 28, 2006, the disclosures of which are incorporated herein by reference.

TECHNICAL FIELD

The present invention relates to a micro plate treating device and a micro plate treating method.

BACKGROUND ART

The micro plate is a member wherein pluralities of wells, which can hold liquid, are arranged in a matrix form (row and column form). Known are, for example, 4 rows×6 columns (=24 wells), 6 rows×8 columns (=48 wells), 8 rows×12 columns (=96 wells), 12 rows×16 columns (=192 wells), and 16 rows×24 columns (=384 wells). The intervals between the individual wells in these micro plates tend to be normalized. In, for example, a micro plate having 96 wells, the row interval thereof, which is the distance in the column direction between the well centers of any one of the rows where some of the wells are arranged and those of the rows where wells adjacent to the wells in the column direction are arranged, and the column interval thereof, which is the distance in the row direction between those of any one of the columns where some of the wells are arranged and those of the columns where wells adjacent thereto in the row direction are arranged, are each 9 mm. In 384 wells, the well number of which is 4 times, the row interval and the column interval are each 4.5 mm.

When these micro plates are used to conduct simultaneous treatment operations, wherein plural kinds of solutions are used in parallel, the following dispensing device was used: a dispensing device wherein a single nozzle head equipped with nozzles the number of which is equal to the number of the individual wells in each of the micro plates or with dispensing tips fitted to the nozzles is used to insert the dispensing tips simultaneously into the individual wells in each of the micro plates and then solutions or suspensions to be handled so as to be equal to each other in kind or amount are sucked or discharged (Patent Document 1).

For example, in the case of causing plural kinds of reagents successively to react with many target substances extracted from many specimens etc. which are to be treated, thereby conducting a series of treatment operations, micro plates each having wells the number of which corresponds to the number of the specimens are prepared by the following number in order to hold, in advance, reagent solutions, specimens, or magnetic particle suspensions required for the treatment: a number corresponding to the number of steps required for the treatment process or the number of the required kinds of the reagents or the like. The dispensing device, which can cause the magnetic particles to be adsorbed on inner walls of the dispensing tips corresponding to nozzles, are used to transfer the magnetic particles successively to the individual wells in plurality of the micro plates, so as to suspend the particles in the wells, thereby causing reaction. These steps are successively performed, thereby conducting the treatment (Patent Documents 1 and 2).

Therefore, when the kinds of the reagents used in the treatment are increased, the number of the micro plates to be used increases since any one of the micro plates is assigned to each of the kinds. Thus, the area for the work increases. The moving distance of the nozzle head corresponds to the distance over which the nozzle head passes all the micro plates the number of which corresponds to the number of the kinds of the reagents or the like required for the treatment; therefore, when the number of the micro plates increases, the moving distance of the nozzle head increases. As a result, there remains a problem that it is feared that the treatment can neither be promptly nor effectively conducted.

When a liquid amount of about one hundred microliters to several hundreds of microliters is merely handled as in the prior art, the liquid amount can be sufficiently used by combining ordinary micro plates with the above-mentioned dispensing device. However, when the liquid amount to be handled is increased so that a liquid amount of about one thousand microliters to several thousands of microliters needs to be handled, it is necessary to increase the volume of each of the wells and further increase the volume of each of the dispensing tips. As a result, when the interval between the wells in the micro plates is normalized, the height of the micro plates increases and further the length of the dispensing tips in the axial direction thereof increases, so that the scale of the device is enlarged in the vertical direction. Thus, there remains a problem that is feared that the device may not be easily handled in order to attain the transfer of the nozzle head, or the like.

Furthermore, when the number of parallel treatment operations for handling specimens in parallel is increased, number of the wells in the micro plates increases: thus, necessity that the wells should be highly integrated increases. Accordingly, the individual nozzles need to be arranged closely to each other. Thus, the interval between the dispensing tips is made narrow so that the area occupied by each of the dispensing tips becomes narrow. As a result, there is caused a problem that is feared that functions to be adopted by the dispensing tips are unavoidably lowered.

[Patent Document 1:] International Publication WO 99/47267

[Patent Document 2:] Japanese Patent No. 3115501

DISCLOSURE OF THE INVENTION

Problems to be Solved by the Invention

Thus, the present invention has been made in order to solve the above-mentioned problems, and a first object thereof is to provide a micro plate treating device and a micro plate treating method capable of handling a larger number of kinds of solution or suspensions or a larger volume of solutions or suspensions per work area or per volume of the device by use of a normalized micro plate without enlarging the scale of the device. A second object thereof is to provide a micro plate treating device and a micro plate treating method capable of conducting treatment more promptly and more effectively in the case of making the number of wells and the number of nozzles unchanged. A third object thereof is to provide a micro plate treating device and a micro plate treating method having a high functionality even when the number of treating-targets to be handled in parallel is made large.

Means for Solving the Problems

A first aspect of the invention is a micro plate treating device, comprising a micro plate having wells arranged in a matrix form, one or more nozzle heads each having nozzles capable of sucking and discharging a fluid and arranged in a matrix form, and moving means capable of moving relatively an interval between the micro plate and the nozzle heads, wherein tips of all the nozzles arranged in each of the nozzle heads are configured to be permitted to be simultaneously inserted into some of the wells in the micro plate, at least one of the row interval or the column interval of the nozzles is set to two or more natural number multiple of the row interval or the column interval of the corresponding wells (i.e., the corresponding ones out of the wells), the natural number being two or more, and at least one of the row number or the column number of all the corresponding nozzles is one to the natural number of the row number or the column number of the wells.

Herein, the "matrix form" refers to a structure wherein along two directions of a column direction and a row direction, elements such as wells or nozzles are arranged at a predetermined row interval and a predetermined column interval, the number of the rows is a predetermined number, and the number of the columns is a predetermined number respectively. The number of the rows and the number of the columns are each two or more. The column direction and the row direction are usually orthogonal to each other, but are not limited thereto. Thus, the directions may be obliquely intersected. The matrix form also include a case in which in individual rows or columns adjacent to each other, for example, the row or columns are shifted from each other by a length of a half of the column interval or the row interval so that the elements are alternated, thereby arranging the elements into a closed-pack form. The "row interval" means the distance in column direction between the center of any one out of elements arranged in a matrix form or a centerline of the row in which the element is arranged and the center of an element adjacent thereto in the column direction or the centerline of the row in which the element is arranged. The "column interval" means the distance in row direction between the center of any one out of elements arranged in a matrix form or a centerline of the column in which the element is arranged and the center of an element adjacent thereto in the row direction or the centerline of the column in which the element is arranged.

The "nozzles" are parts for sucking and discharging a fluid, and examples of the fluid include gas and liquid. The nozzles are each a cylinder having a plunger, or a channel connected to a mechanism for sucking and discharging a fluid by deformation of bellows or an elastomer. Examples of the nozzles include channels in dispensing tips fitted to fitting nozzles.

Since "the tips of all the nozzles are configured to be permitted to be simultaneously inserted into some of the wells in the micro plate", it is generally necessary that: the row number or the column number of the matrix of the nozzles is smaller than that of the matrix of wells; the angle made between the row direction and the column direction in the matrix of the nozzles is equal to that in the matrix of the wells; and the row interval or the column interval of the matrix of the nozzles is a natural number multiple of the row interval or the column interval of the matrix of the wells.

Since "at least one of the row interval or the column interval of the nozzles is set to a natural number multiple of the row interval or the column interval of the corresponding wells [=natural number times the row interval or the column interval of the corresponding wells], the natural number being two or more, and at least one of the row number or the column number of the corresponding nozzles is one to the natural number of the row number or the column number of the wells [=1/(the natural number of the row number or the column number of the wells)]", the following is inevitably present in the micro plate: matrix form arrangements of nozzles which each have the same configuration as the arrangement of the wells in a matrix form and which do not overlap with each other, the number of the arrangements being at least natural number (>1) (the arrangements will be referred to as "partial well matrices" hereinafter). Additionally, any one of the well elements belonging to any one of the partial well matrices and the corresponding one of the well elements belonging to any one of the partial well matrices adjacent thereto are not separated from each other by not less than the distance between any adjacent ones out of the wells in the micro plate.

In this way, the area for work can be limited to the inside of the single micro plate having an area substantially consistent with that of the nozzle head although the well groups which are independent and which the nozzle heads can be simultaneously inserted into are present in a number of two or more; thus, the work area is not enlarged in vain. About the movement of the nozzle head between the partial well matrices, the tips of all of the nozzles of the nozzle head can be positioned to be permitted to be inserted into all the partial well matrices in the micro plate by repeating a movement corresponding to at longest the distance of the row interval or the column interval at least ((N−1) times wherein N is a natural number (>1)).

Since the natural number is two or more, it is necessary that at least either one of the row number or the column number of the wells in the micro plate is a number having this natural number (>1) as a divisor thereof. About, for example, a nozzle head having nozzles arranged to have a column interval 3 times larger than that of a micro plate having wells arranged in a matrix form of 4 rows×12 columns, the natural number corresponds to "3". The column number of the nozzles is 4, which is 1/"3" of 12, which is the column number of the wells. In such a way, 12 of the column number of the wells has "3" as a divisor thereof.

A second aspect of the invention is the micro plate treating device which further comprises a control unit, wherein the control unit causes the moving means to attain the relative movement between the nozzle head and the micro plate, thereby causing the tips of all the nozzles fitted to the nozzle head to be positioned in such a manner that the tips can be simultaneously inserted into the wells belonging to a first partial well matrix, which is the corresponding partial well matrix, in the micro plate, inserting the tips of the nozzles simultaneously into the wells so that a treatment operation is conducted, pulling out the tips; and then causes the moving means to attain the relative movement between the nozzle head and the micro plate, thereby causing the tips of all the nozzles to be positioned in such a manner that the tips can be simultaneously inserted into the wells belonging to a second partial well matrix, which is the corresponding partial well matrix, in the micro plate.

The reason why the above has described only a case where the device has the "first partial well matrix" and the "second partial well matrix" is that the number of the partial well matrices is at least the natural number (n>1). In a case where the wells in the micro plate have an ordinary matrix form configuration, all the nozzles can be inserted into all the partial well matrices in the micro plate by carrying out relative movement between by at least the natural number (n>1 time) the nozzle head and the micro plate along the corresponding column direction and/or row direction by the distance of the row interval or column interval of the wells in the micro plate. The "first partial well matrix" and the "second partial well matrix" do not have wells overlapping with each other.

In a case where the row interval and the column interval of the nozzles are a natural number (n>1) multiple of the row interval of the wells and a natural number (m>1) multiple of the column interval of the wells, respectively, the number of the partial well matrices is nm in total for the single micro plate. Examples of the "treatment" include suction of the fluid from the wells or discharge thereof into the wells, repetition of the suction and the discharge, adsorption of magnetic particles contained in a liquid onto inner walls of the nozzles by applying a magnetic field to the nozzles, re-suspension of the magnetic particles by removing the magnetic field, and detection of a liquid amount.

A third aspect of the invention is the micro plate treating device, wherein individual partial well matrices along a moving path of the nozzle head hold solutions or suspensions necessary for individual steps of the treatment in accordance with the order of the steps.

Herein, the "moving path" is a path through which the nozzle head passes when the nozzle head is moved successively parallel over all the partial well matrices, and is preferably a path the distance of which is the shortest along the moving course. Accordingly, selection from the individual partial well matrices is made in accordance with the order of the treating steps, and then necessary solutions, such as reagents, and others are put thereto. In general, solutions or suspensions to be handled so as to be equivalent to each other in kind or amount are put in the wells in the same (i.e., single one) belonging to out of the partial well matrices, and solutions or suspensions to be handled so as to be different from each other in kind or amount are put in the wells belonging to any different ones out of the partial well matrices. This is because sucking or discharging operations of the individual nozzles fitted to be equivalent nozzle heads are linked to each other so that the individual operations are substantially identical. Alternatively, in the case of handling a liquid in a great volume, solutions or suspensions equivalent to each other in kind may be put in the wells belonging to different ones out of the partial well matrices.

A fourth aspect of the invention is the micro plate treating device, wherein the control unit causes the nozzle head to be successively moved so as to position the tips of the nozzles in the state that the tips can be inserted into all the wells belonging to each of the well groups, in the micro plate, into which the tips of the same nozzles fitted to the nozzle head can be inserted.

Each of the well groups includes one unit of each of well elements belonging to each of the partial well matrices, so as to avoid the overlap of two or more units thereof. Accordingly, the element number of the wells belonging to each of the well groups is equal to the number of the partial well matrices present in the single micro plate. In other words, according to this manner, the individual nozzles are in the state that the nozzles can be simultaneously inserted into the corresponding each of the wells in all the well groups. The number of the wells belonging to each of the well groups is at least the natural number (n>1). When the row interval and the column interval of the nozzles are natural number multiples (n>1, and m>1) of the row interval and the column interval of the wells, respectively, the number of the wells belonging to each of the well groups is nm. The moving path of each of the nozzles inside the well groups is a path permitting the nozzle to pass through all the well elements in the well groups in accordance with the order of the treating steps, and is preferably a path the distance of which is the shortest.

A fifth aspect of the invention is the micro plate treating device, wherein partitions for partitioning the well groups, in the micro plate, into which the same nozzles fitted to the nozzle head can be inserted from each other are built on the upper surface of the micro plate so as to be projected therefrom.

According to this manner, for example, a large number of specimens to be treated can be treated in the state that the specimens are partitioned from each other with the partitions; therefore, once the nozzles are moved into one of areas surrounded by the partitions, the treatment can be conducted without shifting the tips of the nozzles over any one of the partitions.

A sixth aspect of the invention is the micro plate treating device, wherein the number of the nozzle heads and the number of the micro plate and one or more optional micro plates equivalent thereto are each at least the natural number. At this time, the individual nozzle heads can be set up or controlled to cause the operations of the heads to be linked with each other.

A seventh aspect of the invention is the micro plate treating device, wherein the nozzle head is provided with magnetic force means having two or more magnets which can be brought into contact with the nozzles and be separated from the nozzles, so that a magnetic field can be applied simultaneously to the inside of the nozzles and be further removed therefrom.

An eighth aspect of the invention is the micro plate treating device, wherein: the magnetic force means comprises plural comb teeth members that can be moved relatively to the nozzle heads, wherein nozzle rows having the nozzles arranged along the row direction and nozzle columns having the nozzles arranged along the column direction are arranged, along the row direction or the column direction, that extend along the row direction or the column direction, at least one of the members having a width permitted to be inserted in the nozzle row interval or the nozzle column interval, and that each have a length adjacent to all the nozzles in one or two of the nozzle rows or the nozzle columns when the members are inserted therein, and a supporting member connected to the comb teeth members; and the magnets that are arranged at the column interval or row interval at positions corresponding to adjacent ones of the individual nozzles are fitted to each of the comb teeth members. The nozzle row interval or the nozzle column interval has, for example, a row interval or column interval set to a natural number multiple of the row interval or column interval of the wells, the natural number being two or more. When the comb teeth members can be inserted into individual gaps between the nozzle rows or between the nozzle columns, the required comb teeth members are comb teeth members the number of which is (the number of nozzle rows−1) or (the number of nozzle columns−1). Allowable are comb teeth members adjacent to the nozzle rows or nozzle columns in the state that the members are not inserted in gaps between the nozzle rows or between the nozzle columns. The distance between any one of the magnets and the nozzles adjacent to the magnet is a range permitting a magnetic field necessary for the treatment operation to be applied to the nozzles. The supporting member is, for example, a member for connecting the comb teeth members to each other at single-ends of the comb teeth members at the backside of the nozzle-advancing direction. About any one of the comb teeth members, in the width direction thereof, magnets maybe arranged at each side thereof at the column interval or row interval, correspondingly to any two adjacent ones of the nozzle rows or any two adjacent ones of the nozzle columns at each side of the width direction.

A ninth aspect of the invention is the micro plate treating device, wherein the nozzle head further comprises light-detecting means for detecting the state of the liquid in the nozzles. It is therefore necessary that the nozzles or dispensing tips fitted to fitting nozzles are made of a translucent member or translucent members. Examples of the "the state of liquid" include the presence or absence of the liquid, and the suction amount or the discharge amount of the liquid.

A tenth aspect of the invention is the micro plate treating device wherein: the light-detecting means comprises plural light-detecting comb teeth members that can be moved relatively to the nozzle heads, wherein nozzle rows having the nozzles arranged along the row direction and nozzle columns having the nozzles arranged along the column direction are arranged, along, the row direction or the column direction, that extend along the row direction or the column direction, at least one of the members having a width permitted to be inserted in the nozzle row interval or the nozzle column interval, and that each have a length adjacent to all the nozzles in one or two of the nozzle rows or the nozzle columns when the members are inserted therein, and a supporting member connected to the light-detecting comb teeth members; and at least one light-detecting unit is set up to each of the light-detecting comb teeth members.

The nozzle row interval or the nozzle column interval has, for example, a row interval or column interval set to a natural number multiple of the row interval or column interval of the wells, the natural number being two or more. When the comb teeth members can be inserted into the individual gaps between the nozzle rows or between the nozzle columns, the required comb teeth members are light-detecting comb teeth members the number of which is (the number of nozzle rows−1) or (the number of nozzle columns−1). The light-detecting comb teeth members may be positioned outside the nozzle rows or the nozzle columns. The supporting member is, for example, a member for connecting the light-detecting comb teeth members to each other at single-ends of the comb teeth members.

An eleventh aspect of the invention is a micro plate treating method, comprising a first step of preparing a micro plate having wells arranged in a matrix form, and one or more nozzle heads each having nozzles capable of sucking and discharging a liquid and arranged in a matrix form, and moving, relatively to the micro plate, the nozzle heads wherein at least one of the row interval or the column interval of the nozzles is set to a natural number multiple of the row interval or the column interval of the corresponding wells, the natural number being two or more, and at least one of the row number or the column number of the corresponding nozzles is one to the natural number of the row number or the column number of the wells, thereby positioning all the nozzles fitted to each of the nozzle heads in such a manner that all the nozzles can be simultaneously inserted into the wells belonging to a first partial well matrix in the micro plate; and a second step of attaining relative movement between the nozzle heads and the micro plate, thereby positioning tips of all the nozzles in such a manner that the tips can be simultaneously inserted into the wells belonging to a second partial well matrix, which is the corresponding partial well matrix, in the micro plate.

The reason why the above has described only a case where the method has the "first step" and the "second step" is that the number of the partial well matrices is at least the natural number (n>1). Accordingly, in a case where the row interval and the column interval of the nozzles are a natural number (n>1) multiple of the row interval of the wells and a natural number (m>1) multiple of the column interval of the wells, respectively, the number of the partial well matrices is nm in total for the single micro plate. The number of steps therefore is nm in total for the single micro plate.

In the case of an ordinary matrix form configuration, all the nozzles can be simultaneously inserted into all the partial well matrices in the micro plate by carrying out relative movement between the nozzle head and the micro plate along the corresponding column direction or row direction by the distance of the row interval or column interval of the wells in the micro plate at least natural number times (n>1).

A twelfth aspect of the invention is the micro plate treating method, wherein the first step comprises the step of treatment inserting the nozzles to the individual wells, thereby attaining the treatment operation, and the step of pulling out the nozzles from the wells. The second step also may have an inserting step, a treating step, or a pulling-out step in the same manner as the first step. The step number required is decided in accordance with at least the set natural number (n>1). Steps the number of which is at least the natural number times are required. The "treatment" referred to herein is as described above.

A thirteenth aspect of the invention is the micro plate treating method, wherein the first or second step comprises the step of applying a magnetic field to the inside of the nozzles and the step of removing the magnetic field at the time of the suction or discharge.

A fourteenth aspect of the invention is the micro plate treating method, wherein the first or second step comprises the step of detecting the state of the liquid in the nozzles.

Effects of the Invention

According to the first aspect of the invention, at least one of the row interval or column interval of the nozzles is a natural number multiple of the row interval or column interval of the corresponding wells, the natural number being two or more; therefore, two or more of the wells can be caused to correspond to one of the nozzles. Accordingly, without setting up any new micro plate, two or more kinds of solutions or the like can be handled in the single micro plate. As a result, a larger number of kinds of solutions or the like can be handled without increasing the area for work.

Moreover, any one of the nozzles can correspond to two or more of the wells; therefore, a liquid having a volume two or more times larger than the volume handled by any one of the wells can be handled by any one of the nozzles. Furthermore, usable large spaces make their appearance between adjacent ones of the nozzles; therefore, each of the nozzles can be provided with mechanisms for giving various functions, such as a function of applying magnetic force into the nozzle, and a function of detecting the state of the liquid in the nozzle or the like, without enlarging the scale of the device.

The second or eleventh aspect of the invention produces the advantageous effects of the first aspect of the invention. Besides, the wells which can be handled at a time by any one of the nozzle heads correspond to each of the partial well matrices which belong to the single micro plate and do not overlap with each other, and further the individual partial well matrices are apart from each other only by a distance corresponding to the distance between the wells adjacent to each other in the micro plate; therefore, when a solution or the like that is necessary for a single treatment operation is put into each of the partial well matrices, it is sufficient that the moving distance of the nozzle head which permits the single treatment operation to be completed is short. Thus, the treatment operation can be promptly and effectively conducted.

According to the third aspect of the invention, for the single micro plate, any one of the nozzle heads is used to make it possible to conduct a series of treatment operations, for many objects to be treated, composed of plural steps continuously to the last; therefore, the treatment efficiency is high for the work area. Additionally, it is sufficient that the moving distance of the nozzle head is short; thus, the working efficiency is high.

According to the fourth aspect of the invention, each of the well groups includes one unit of each of well elements belonging to each of the partial well matrices, so as to avoid the overlap of two or more units thereof. Therefore, when the nozzles are moved in such a manner that the nozzles can be inserted to all the wells belonging to the well group, a series of treatment operations composed of steps the number of which is at least the natural number (n>1) can be continuously applied to a large number of objects in the single micro plate to the last inside the single micro plate; thus, the device is high in reliability and is easily controlled.

According to the fifth aspect of the invention, by surrounding a group of the wells in which a treatment operation is applied to one object through any one of the nozzles by the partitions, the treatment operation based on the single nozzle is finished inside the partitions. Thus, the treatment can be conducted without shifting the tip of the nozzle over the partitions. Therefore, cross contamination over the partitions can be certainly prevented. Moreover, the individual nozzles are each moved inside the partitions. Thus, the control of the movement is easy.

According to the sixth aspect of the invention, the total number of the nozzles fitted to the nozzle heads the number of which is at least the natural number can be made equal to the number of wells in any one of the micro plates, and the number of the nozzle heads can be made equal to the number of the micro plates. Accordingly, the moving distance of the nozzle heads becomes remarkably small although the total number of the nozzles of the nozzle heads is substantially equal to the number of the wells in any one of the micro plates. However, simultaneous treatment operations in the micro plates can be conducted; thus, the number of objects to be treated is maintained, and each of the micro plates has partial well matrices the number of which is at least the natural number. For this reason, the nozzle heads can be used plural times for any one of the micro plates.

According to the seventh or thirteenth aspect of the invention, a magnetic field can be applied to the nozzles; therefore, a suspension wherein magnetic particles are suspended in the wells in the micro plate are used and the particles can be adsorbed on inner walls of the nozzles so as to be separated. As a result, various treatments can be conducted.

According to the eighth aspect of the invention, magnets which may have an intense magnetic force can be set up by use of the gaps between adjacent ones of the nozzle rows or adjacent ones of the nozzle columns, which have the row interval or column interval of the nozzles fitted to the nozzle head, which is set to the natural number multiple of the row interval or column interval of the wells, the natural number being two or more. Therefore, even when the micro plate is a micro plate wherein wells are densely integrated, an intense magnetic field can be applied to the individual nozzles and removed therefrom by means of a simple mechanism.

According to the ninth aspect or fourteenth aspect of the invention, the sucking or discharging state of the liquid can be measured by detecting the states of the insides of the nozzles. Thus, a control high in reliability can be made.

According to the tenth aspect of the invention, a light-detecting unit can be set up by use of the gaps between adjacent ones of the nozzle rows or adjacent ones of the nozzle columns, which have the row interval or column interval of the nozzles fitted to the nozzle head, which is set to the natural number multiple of the row interval or column interval of the wells, the natural number being two or more. Therefore, even when the micro plate is a micro plate wherein wells are densely integrated, the individual states of the nozzles can be certainly and effectively detected. Thus, a control high in reliability can be made.

According to the twelfth aspect of the invention, even the single micro plate can cope with plural steps using plural kinds of solutions or the like by applying simultaneous insertion, suction, discharge and pulling-out repeatedly to the partial well matrices present in the micro plate. Accordingly, the plural steps can be carried out without enlarging the area for work.

BEST MODE FOR CARRYING OUT THE INVENTION

Micro plate treating devices and micro plate treating methods according to embodiments of the invention will be described hereinafter on the basis of the drawings.

Figure 1:
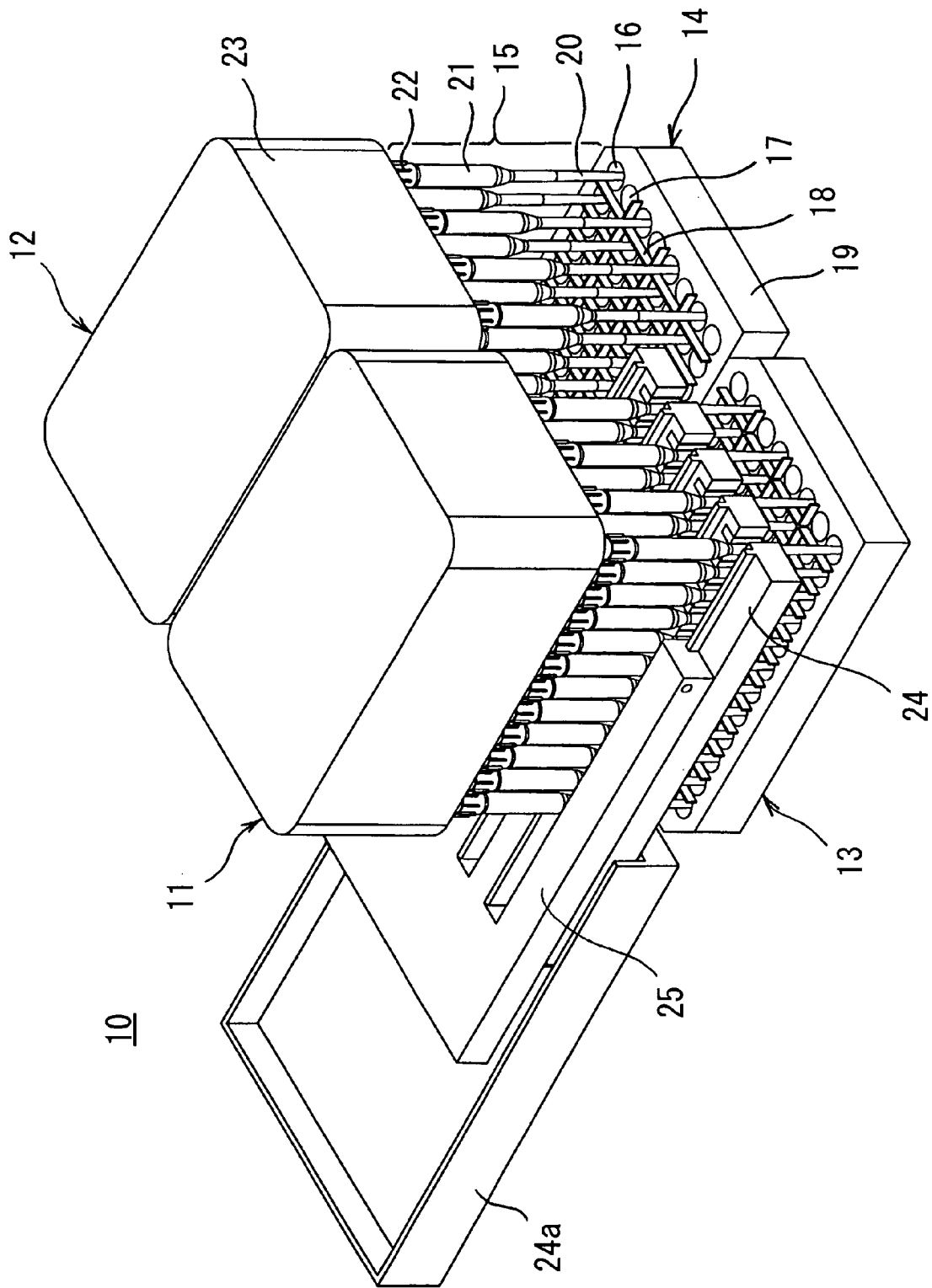
FIG. 1 is a perspective view illustrating the micro plate treating device according to the first embodiment of the invention.

FIG. 1 is a perspective view of a micro plate treating device 10 according to a first embodiment of the invention. The micro plate treating device 10 has two micro plates 13 and 14 wherein wells are arranged in a matrix form, two nozzle heads 11 and 12 each having dispensing tips 15, as nozzle parts, fitted to nozzles which can suck and discharge fluids and are arranged in a matrix form, moving means (not illustrated) for moving the interval between the micro plates 13 and 14 and the nozzle heads 11 and 12 relatively, comb teeth magnets 24 as magnetic force means for applying a magnetic field to the insides of the dispensing tips 15, and comb teeth light-detecting units 25 as light-detecting means for detecting the states of the liquids in the dispensing tips 15. For explanation, one of the comb teeth magnets 24 and one of the comb teeth light-detecting units 25 are illustrated only about the nozzle head 11. Reference numeral 24a represents a tray fitted to be fixed to the nozzle head in order to support the comb teeth magnet 24 so as to be movable in the row direction.

In each of the micro plates 13 and 14, 96 openings, i.e., circular wells 16 and 17 are arranged in a matrix form of 8 rows×12 columns in a substrate 19, which is in a rectangular form as a whole. The distances between the wells, that is, the row interval and the column interval are each 9 mm.

The nozzle heads 11 and 12 are arranged to be relatively movable over the micro plates 13 and 14, respectively. The nozzle heads 11 and 12 each have a mechanism unit 23 equipped with cylinders and nozzles connected to the cylinders, as the above-mentioned sucking and discharging mechanism, and the dispensing tips 15 fitted to the nozzles. The dispensing tips 15 each have a large-diameter section 21 and a small-diameter section 20 connected to the large-diameter section 21. A fitting section 22 that is to be fitted to each of the nozzles is fitted to the upper side of the large-diameter section 21. The tips of the small-diameter sections 20 each have a diameter permitted to be inserted into each of the wells 16 and 17 in the micro plates 13 and 14.

The tips of all the dispensing tips 15 arranged in the matrix form of in each of the nozzle heads 11 and 12 are positioned in such a manner that the tips can be simultaneously inserted into some of the wells (i.e., any partial well matrices) in the micro plate 13 or 14. The row interval of the matrix, where the dispensing tips 15 as nozzles are arranged, is set to a "2" multiple, as a natural number multiple, of the row interval of the matrix where the wells 16 and 17 are arranged. The row number, "4", of the dispensing tips 15, as all the corresponding nozzles, is 1 to the natural number of the row number, "8", of the wells, that is, 1/"2". The matrix where the dispensing tips 15 are arranged is a matrix where tips corresponding to 4 rows of the wells 16 and 17 in the matrix of the micro plate 13 and 14 are thinned out so that the dispensing tips 15 of 4 rows×12 columns, the number of which is 48, are arranged. Accordingly, the number of the dispensing tips 15 of each of the nozzle heads 11 and 12 is 48, so that the number of the dispensing tips 15 in the two nozzle heads is 96. The number is equal to the number of the wells in any one of the micro plates.

The material of the micro plates is, for example, a resin such as polyethylene, polypropylene, polyester, polystyrene, polyvinyl, or acrylic resin. The moving means for the nozzle heads 11 and 12, which is not illustrated, is, for example, a Z axis motor for attaining movement in the vertical direction, and a ball screw mechanism driven rotationally by the motor; an X axis motor for attaining movements in the X axis direction along the row direction of the micro plates 13 and 14, and a ball screw mechanism driven rotationally by the motor; and a Y axis motor for attaining movements in the Y axis direction along the column direction of the micro plates 13 and 14, and a ball screw mechanism driven rotationally by the motor.

Figure 3:
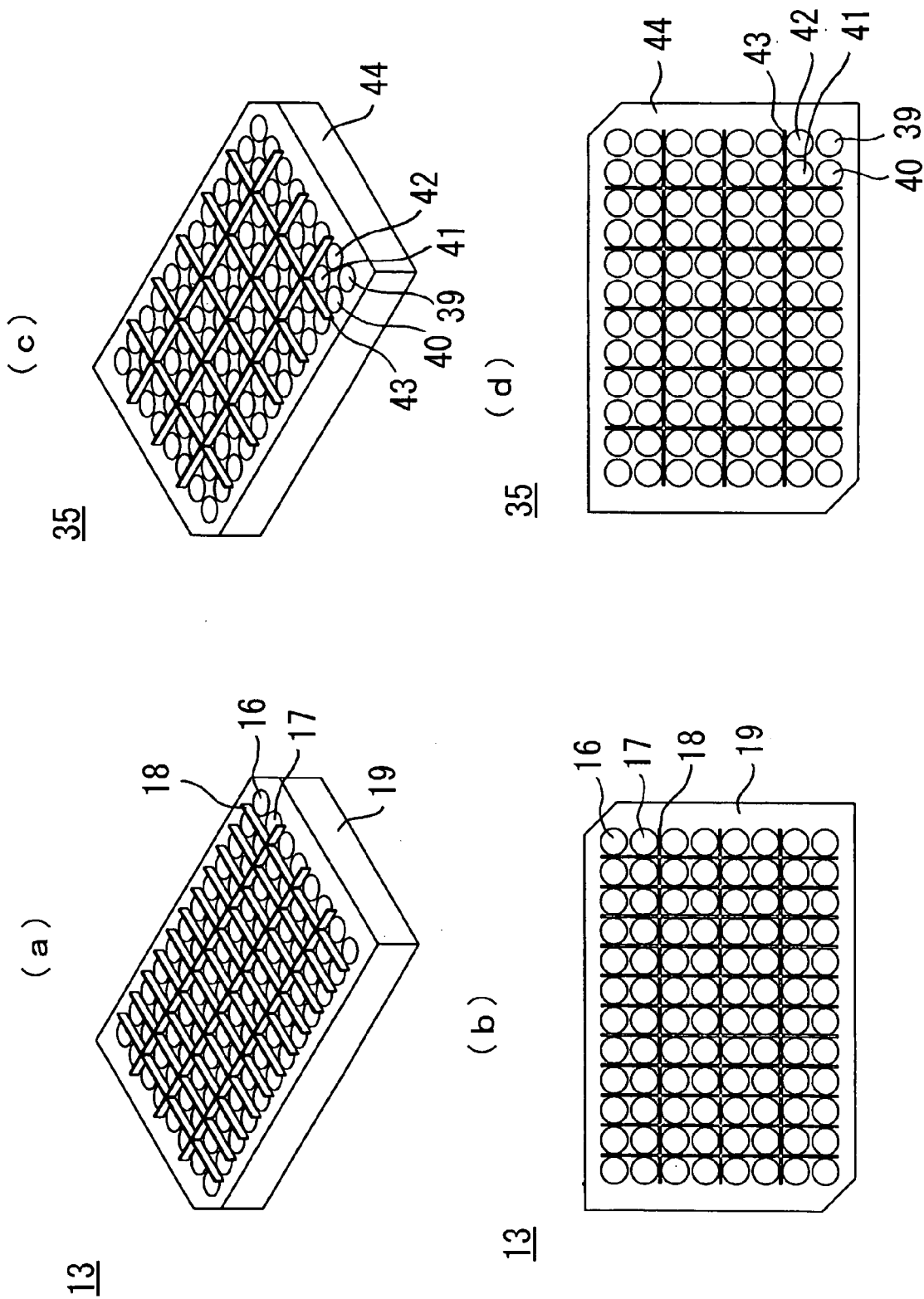
FIG. 3 are views illustrating the micro plates in the embodiments of the invention.

FIGS. 3(a) and (b) are views illustrating the micro plate 13 (14) in detail. The micro plate 13 is a micro plate wherein the wells 16 and 17, the number of which is 96, are arranged in a matrix form of 8 rows×12 columns on the substrate 19. Furthermore, partitions 18, in the form of slender thin plates, are arranged on the surface of the substrate 19 so as to be projected upwards in such a manner that three of the partitions 18 are positioned along the row direction and eleven of the partitions 18 are positioned along the column direction and in such a manner that the partitions 18 cause all the wells to be partitioned into the well groups each made of wells the number of which is the natural number, "2" (i.e., one of the wells 16 and one of the wells 17), which are arranged in the column direction, correspondingly to the row interval of the arranged dispensing tips 15 of the corresponding nozzle head 11.

FIG. 4(a) illustrates a first partial well matrix (the wells 16, represented by white circles in the figure) and a second partial well matrix (the wells 17, represented by black circles in the figure), which are each a group of wells into which all the matrix form dispensing tips 15 of the nozzle head 11 corresponding to the micro plate 13, which are arranged in a matrix form, can be simultaneously inserted. Accordingly, the arrangement of the dispensing tips 15 of the nozzle head 11 has a matrix corresponding to the arrangement of the first partial well matrix (the wells 16) and the second partial well matrix (the wells 17).

Any one group composed of any one of the wells 16 belonging to the first partial well matrix (the wells 16) and represented by one of the white circles, and one of the wells 17 belonging to the second partial well matrix (the wells 17) and represented by one of the black circles which is below the well 16 represented by the white circle and is adjacent thereto in the column direction is a well group 50 that is a group of wells into which the same dispensing tip 15 out of the dispensing tips 15 fitted to the corresponding nozzle head 11 can be inserted. Accordingly, the dispensing tip 15 positioned once in each of areas surrounded by the partitions 18 is not shifted over any one of the partitions 18 until the treatment operations about the micro plates 13 and 14 are completed.

FIG. 5(a) is a perspective view illustrating the comb teeth magnet 24 and the comb teeth light-detecting unit 25, which are in the state that they are taken out. The comb teeth magnet 24 has two or more magnets 61 arranged to be brought into contact with the dispensing tips 15 fitted to the nozzle head 11 and separated therefrom, so as to apply a magnetic field simultaneously to the insides of the dispensing tips 15, as nozzles, and remove the magnetic field.

The comb teeth magnet 24 has: comb teeth members 60 that are arranged in gaps between adjacent rows of the dispensing tips 15 having a row interval set to a "2" multiple, the number "2" being the natural number of the row interval of the wells 16 and 17, so as to be movable along the row direction, that extend along the row direction, and that are fitted to have a width permitted to be inserted in any one of gaps between adjacent rows of the dispensing tips 15, the number of the comb teeth members 60 being 4, which is the row number of the dispensing tips 15; and a supporting member 60a connected to single-ends of the comb teeth members 60 and extending in the column direction. Each of the comb teeth members 60 is equipped with magnets 61 arranged at the column interval, correspondingly to the positions of the dispensing tips 15 as individual nozzles. The number of the magnets 61 is the column number, that is, 12.

In the figure, reference numeral 62 represents a guide rail laid along the longitudinal direction of the comb teeth members 60, that is, the row direction, so as to guide the movement of the comb teeth light-detecting unit 25, which will be described below, arranged on the upper surface of the comb teeth members 60 so as to be movable.

Figure 6:
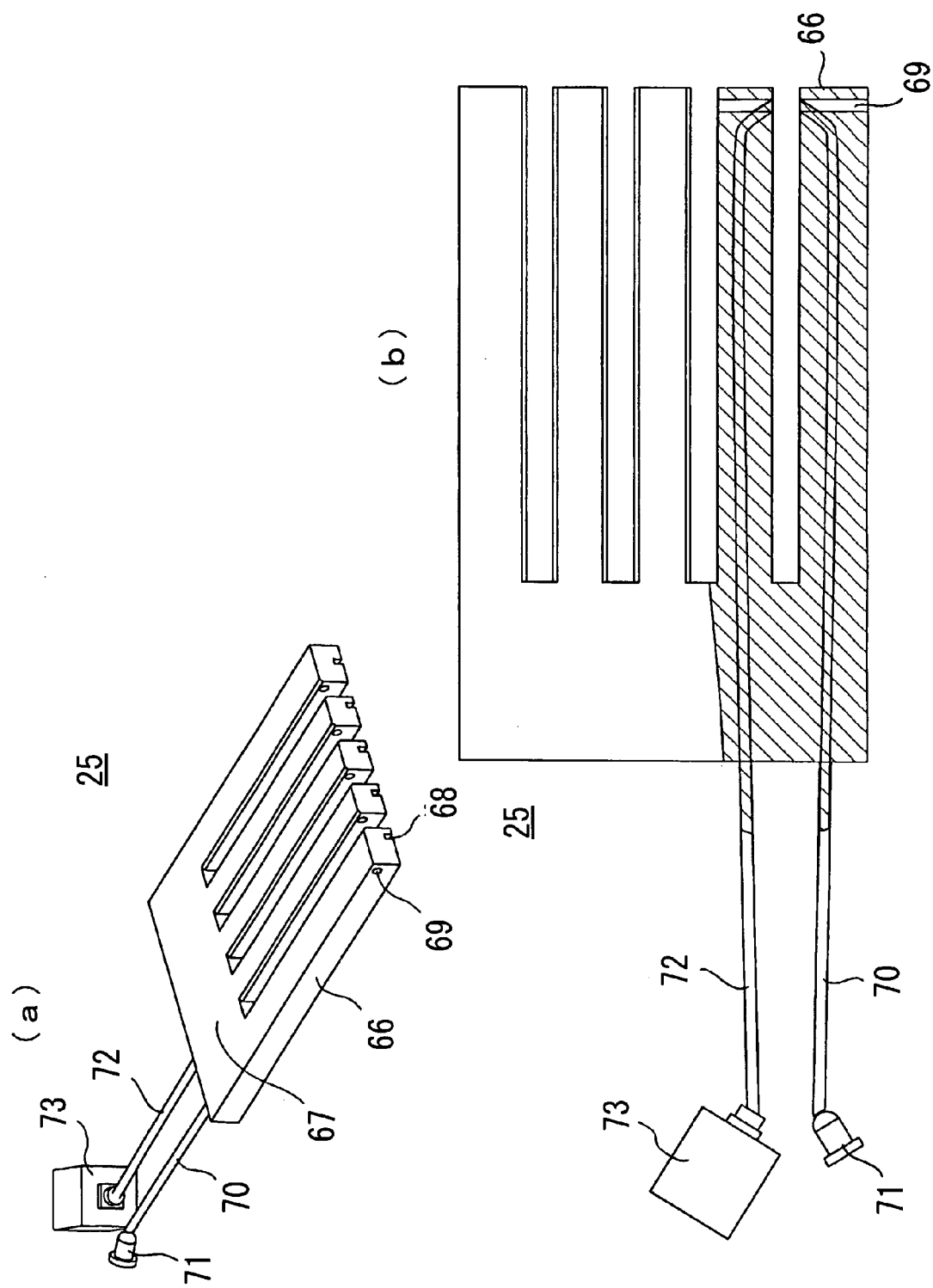
FIG. 6 are views illustrating comb teeth light-detecting units in the embodiments of the invention.

FIG. 6 are views illustrating the comb teeth light-detecting unit 25 in detail. The comb teeth light-detecting unit 25 is a unit arranged on the comb teeth magnet 24 fitted to the nozzle head 11 to be movable to the comb teeth magnet 24, thereby detecting the states of the liquids in the dispensing tips 15.

The comb teeth light-detecting unit 25 has: light-detecting comb teeth members 66 that are arranged in gaps between adjacent rows of the dispensing tips having a row interval set to a "2" multiple, which is the natural number of the row interval of the wells 16 and 17, so as to be movable along the row direction to the comb teeth magnet 24 or the dispensing tips 15, that extend along the row direction, and that are fitted to have a width permitted to be inserted in any one of gaps between adjacent rows of the dispensing tips 15, the number of the light-detecting comb teeth members 66 being 4, which is the row number of the dispensing tips 15; and a supporting member 67 connected to single-ends of the light-detecting comb teeth members 66 and extending in the column direction. In each of the light-detecting comb teeth members 66, a single light-detecting hole 69 is made along the column direction.

To the light-detecting hole 69 made in any one of the light-detecting comb teeth members 66 is fitted a tip of an optical fiber from a light-emitting unit 71. To the light-detecting hole 69 in the light-detecting comb teeth member 66 adjacent thereto is fitted a tip of an optical fiber 72 connected to an optical sensor 73, so as to face a space where the dispensing tip 15 sandwiched between the two light-detecting comb teeth members 66 is to be arranged.

Reference numeral 68 represents a groove made in each of the light-detecting comb teeth members 66 along the row direction, so as to be slide with being engaged with the guide rail 62.

The micro plate treating device 10 according to the embodiment has a control unit, not illustrated, for controlling operations of the sucking and discharging mechanism, the moving means, the magnetic force means, or the light-detecting means. The control unit has a data processing device having a CPU and a memory for storing, for example, a program and data for making operations in accordance with instructions; a display section such as a display for displaying the states of the operations, instructing command data, input data, or processed result data; inputting means, such as a keyboard or mouse, through which instructing commands or data are input; and outputting means, such as a printer, an external memory, or a communicating device for outputting the processed result data.

The following will describe the operation of the micro plate treating device 10 according to the first embodiment, giving, as an example, a treatment for extracting a nucleic acid such as DNA from specimens, for which the two micro plates 13 and 14 are used, by use of only the nozzle head 11.

Suspensions of specimens and reagent solutions, which are necessary for the treatment, are put beforehand in the wells 16 and 17 in each of the micro plates 13 and 14. For example, as illustrated in FIG. 4(a), about the micro plate 13 having the wells of 8 rows×12 columns, the number of which is 96, the partial well matrix (the wells 16) of 4 rows×12 columns, composed of the wells 16 represented by the white circles, and the partial well matrix (the wells 17) of 4 rows×12 columns, composed of the wells 17 represented by the black circles, are used as units to put 48 specimens such as bloods collected from 48 subjects, as objects to be treated, beforehand in the partial well matrix (the wells 16) to which the wells 16 represented by the white circles belong, and put, for example, suspensions where magnetic particles having, on their surfaces, function groups that can be bonded to the target object material beforehand in the partial well matrix (the wells 17) to which the other wells 17, represented by the other black circles micro plate 13, belong.

Moreover, in the individual partial well matrices (the wells 16 and the wells 17) to which the wells 16 and 17 represented by the white circles and the black circles, respectively, in the micro plate 14 belong, necessary reagents are put beforehand in such a manner that different kinds of the reagents correspond to the partial well matrices, respectively. The nozzle head 11 is moved by the moving means, so as to position the 48 individual dispensing tips 15 in such a manner that the tips 15 can be inserted into the partial well matrix (the wells 17) to which the wells 17 represented by the corresponding black circles in the micro plate 13 belong, in which the specimens are put. All the 48 dispensing tips 15 are simultaneously inserted into all the wells 17 belonging to the partial well matrix (the wells 17), and then the suspensions of the magnetic particles are sucked.

Whether or not the suction is attained is based on the following: the light-detecting comb teeth members 66 of the comb teeth light-detecting unit 25 fitted to the nozzle head 11 are moved in the row direction, whereby the optical sensors 73 receive light rays radiated from the light emitting units 71 and transmitted through the dispensing tips 15, about the states of the liquids in the individual dispensing tips 15, so as to measure the presence or the absence of each of the liquids. Next, the nozzle head 11 is moved upwards to pull out the dispensing tips 15 from the partial well matrix (the wells 17) to which the wells 17 represented by the black circles in the micro plate 13 belong, and then the tips 15 are moved along the column direction by the row interval. In this way, the 48 tips 15 are positioned in such a manner that the tips 15 can be simultaneously inserted into the partial well matrix (the wells 16) to which the wells 16 represented by the white circles belong. Then, all the 48 dispensing tips 15 are simultaneously inserted into all the wells 16 corresponding to the partial well matrix (the wells 16), so as to discharge the suspensions of the magnetic particles into the individual specimen suspensions.

Such a suction and a discharge are repeated. Thereafter, all the liquids are sucked, and then the dispensing tips 15 are pulled out from all the wells in the partial well matrix. Thereafter, the nozzle head 11 or the micro plates 13 and 14 are moved to shift the micro plate 14 below the nozzle head 11.

Similarly, all the dispensing tips 15 are moved in such a manner that the tips 15 can be inserted into the wells 16 in the partial well matrix (the wells 16) to which the wells 16 represented by the white circles in the micro plate 14 belong. Then, all the dispensing tips 15 are simultaneously inserted into all the wells 16 in the partial well matrix (the wells 16), and then the specimens and the magnetic-particle-mixed suspensions are discharged thereinto, so as to cause them together with, for example, a reagent in which the specimens can be dissolved out of the above-mentioned reagents to react with each other. In this way, DNA or the like is extracted from the specimens, and then bonded to the magnetic particles.

Such a suction and a discharge through the dispensing tips 15 are repeated, and then the comb teeth members 60 of the comb teeth magnet 24 fitted to the nozzle head 11 are moved to be inserted into gaps between the rows of the dispensing tips 15, so as to cause the individual magnets 61 to approach the outer side surfaces of the individual dispensing tips 15. A magnetic field is then applied to the insides of the individual tips 15 from the external. In this state, such a suction and a discharge are repeated to cause the magnetic particles to be adsorbed onto inner walls of the dispensing tips 15. In this way, the magnetic particles are separated.

Next, in the state that the magnetic field is applied to the insides of the individual dispensing tips 15 from the comb teeth magnet 24 to cause the magnetic particles to be adsorbed thereon, the dispensing tips 15 are pulled out from the individual wells 16 in the partial well matrix (the wells 16). The nozzle head 11 is then moved in the column direction by the row interval so as to move all the dispensing tips 15 fitted to the nozzle head 11 in such a manner that the all tips 15 can be inserted into the partial well matrix (the wells 17) to which the wells 17 represented by the black circles in the micro plate 14 belong. Then, all the dispensing tips 15 are simultaneously inserted into all the wells 17 in the partial well matrix (the wells 17), and then the comb teeth magnet 24 is moved to separate the individual magnets 61 from the dispensing tips 15, thereby removing the magnetic field. A suction and a discharge are repeated, together with disassociating liquid held in the wells 17 in the partial well matrix (the wells 17), thereby attaining re-suspension. A magnetic field is again applied thereto, so as to cause only the magnetic particles to be adsorbed onto the inner walls of the dispensing tips 15, whereby the magnetic particles are removed. In this way, the target nucleic acid, such as DNA, can be extracted. In this treatment, therefore, treatment operations for which four micro plates each having 48 wells of 6 rows×8 columns that are completely independently configured are required can be attained by only treatment operations with the two micro plates 13 and 14, which each have 96 wells of 8 rows×12 columns. Thus, for example, in a case where the four micro plates, which each have 48 wells, are arranged in the row direction, the moving distance of the nozzle head 11 is a distance corresponding to about 3×6 rows. However, in a case where the two micro plates, which each have 96 wells, are arranged in the row direction, it is sufficient that the moving distance is a distance corresponding to about 1×8 rows. This distance difference becomes larger as the number of treatment operations is made larger.

Figure 2:
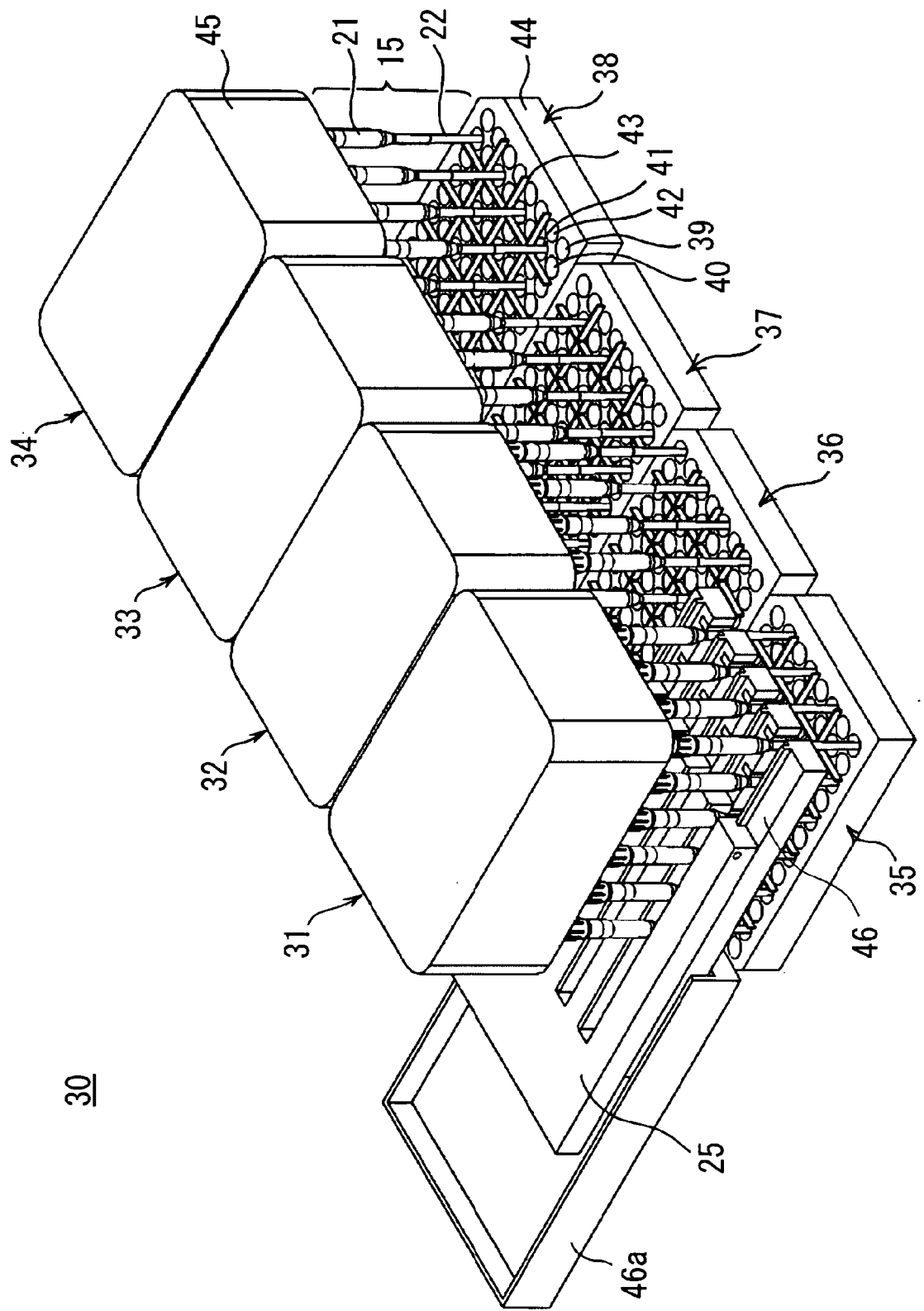
FIG. 2 is a perspective view illustrating the micro plate treating device according to the second embodiment of the invention.

Next, FIG. 2 is illustrated a perspective view of a micro plate treating device 30 according to a second embodiment of the invention. The micro plate treating device 30 has four micro plates 35, 36, 37 and 38 wherein wells are arranged in a matrix form, 4 nozzle heads 31, 32, 33 and 34 each having dispensing tips 15, as nozzle parts, fitted to nozzles which can suck and discharge fluids and are arranged in a matrix form, moving means (not illustrated) for moving the interval between the micro plates 35, 36, 37 and 38 and the nozzle heads 31, 32, 33 and 34 relatively, comb teeth magnets 46 as magnetic force means for applying a magnetic field to the insides of the dispensing tips 15, and comb teeth light-detecting units 25 for detecting the states of the liquids in the dispensing tips 15. For explanation, one of the comb teeth magnets 46 and one of the comb teeth light-detecting units 25 are illustrated only about the nozzle head 31. Reference numeral 46a represents a tray fitted to be fixed to the nozzle head 31 in order to support the comb teeth magnet 46 so as to be movable in the row direction.

In each of the micro plates 35, 36, 37 and 38, 96 openings, i.e., circular wells 39, 40, 41 and 42 are arranged in a matrix form of 8 rows×12 columns in a substrate 44, which is in a rectangular form as a whole. The distances between the wells, that is, the row interval and the column interval are each 9 mm.

The nozzle heads 31, 32, 33 and 34 are arranged to be relatively moved over the micro plates 35, 36, 37 and 38, respectively. The nozzle heads 31, 32, 33 and 34 each have a mechanism unit 45 equipped with cylinders and nozzles connected to the cylinders, as the above-mentioned sucking and discharging mechanism, and the dispensing tips 15 fitted to the nozzles. The dispensing tips 15 each have a large-diameter section 21 and a small-diameter section 20 connected to the large-diameter section 21 in the same manner as in the micro plate treating device 10. A fitting section 22 that is to be fitted to each of the nozzles is fitted to the upper side of the large-diameter section 21. The tips of the small-diameter sections 20 each have a diameter permitted to be inserted into each of the wells 39, 40, 41 and 42 in the micro plates 35, 36, 37 and 38.

The tips of all the dispensing tips 15 arranged in the matrix form of in each of the nozzle heads 31, 32, 33 and 34 are positioned in such a manner that the tips can be simultaneously inserted into some of the wells (i.e., any partial well matrix) in the micro plate 35, 36, 37 or 38. The row interval of the matrix, where the dispensing tips 15 as nozzles are arranged, is set to a "2" multiple, as a natural number multiple, of the row interval of the matrix where the wells 39, 40, 41 and 42 are arranged. The row number, "4", of the dispensing tips 15 as all the corresponding nozzles is set to a "2" multiple, as a natural number multiple, of the column number. The row number, "4", of the dispensing tips 15, as all the corresponding nozzles, is 1 to the natural number of the row number, "8", of the wells, that is, 1/"2". The column number, "6", is 1 to the natural number of the column number, "12", of the wells, that is, 1/"2". The matrix where the dispensing tips 15 are arranged is a matrix where tips corresponding to 4 rows and 6 columns of the wells 39, 40, 41 and 42 in the matrix of the micro plate 35, 36, 37 or 38 are thinned out so that the dispensing tips 15 of 4 rows×6 columns, the number of which is 24, are arranged. Accordingly, the number of the dispensing tips 15 of each of the nozzle heads 31, 32, 33 and 34 is 24, so that the number of the dispensing tips 15 in the 4 nozzle heads is 96. The number is equal to the number of the wells in any one of the micro plates.

The material of the micro plates is, for example, a resin such as polyethylene, polypropylene, polyester, polystyrene, polyvinyl, or acrylic resin. The moving means for the nozzle heads 31, 32, 33 and 34 is included known mechanism such as, which is not illustrated, for example, a Z axis motor for attaining movement in the vertical direction, and a ball screw mechanism; an X axis motor for attaining movements in the X axis direction along the row direction of the micro plate 35,36,37,38, and a ball screw mechanism; and a Y axis motor for attaining movements in the Y axis direction along the column direction of the micro plate 35, 36, 37, 38, and a ball screw mechanism.

FIGS. 3(c) and (d) are views illustrating the micro plate 35 (36, 37 or 38) in detail. The micro plate 35 is a micro plate wherein the wells 39, 40, 41 and 42, the number of which is 96, are arranged in a matrix form of 8 rows×12 columns on the substrate 44. Furthermore, partitions 43, in the form of slender thin plates, are arranged on the surface of the substrate 44 so as to be projected upwards in such a manner that three of the partitions 18 are positioned along the row direction and five of the partitions 18 are positioned along the column direction and in such a manner that the partitions 18 cause all the wells to be partitioned into groups each made of wells the number of which is the natural number, "4" (i.e., one of the wells 39, one of the wells 40, one of the wells 41 and one of the wells 42), which are arranged in the column direction and the row direction, correspondingly to the row interval and the column interval of the arranged dispensing tips 15 of the corresponding nozzle head 31.

FIG. 4(b) illustrates a first partial well matrix (the wells 41, each represented by a white circle in the figure), a second partial well matrix (the wells 42, each represented by a single-line in the figure), a third partial well matrix (the wells 39, each represented by a cross in the figure), and a forth partial well matrix (the wells 40, each represented by a black circle in the figure), which are each a group of wells into which all the matrix form dispensing tips 15 of the nozzle head 31 corresponding to the micro plate 35 can be simultaneously inserted. Accordingly, the arrangements of the dispensing tips 15 of the nozzle heads 31, 32, 33 and 34 have a matrix corresponding to the arrangement of the first partial well matrix (the wells 41), the second partial well matrix (the wells 42), the third partial well matrix (the wells 39), and the fourth partial well matrix (the wells 40).

Any one group composed of any one of the wells 41 belonging to the first partial well matrix (the wells 41) and represented by one of the white circles, one of the wells 42 belonging to the second partial well matrix (the wells 42) and represented by one of the single-lines, one of the wells 39 belonging to the third partial well matrix (the wells 39) and represented by one of the crosses, and one of the wells 40 belonging to the fourth partial well matrix (the wells 40) and represented by one of the black circles is a well group 51 that is a group of wells into which the same dispensing tip 15 out of the dispensing tips 15 fitted to the corresponding nozzle head 31, 32, 33 or 34 can be inserted. Accordingly, the dispensing tip 15 positioned once in each of areas surrounded by the partitions 43 is not shifted over any one of the partitions 43 until the treatment operations about the micro plates 35, 36, 37 and 38 are completed.

Figure 5:
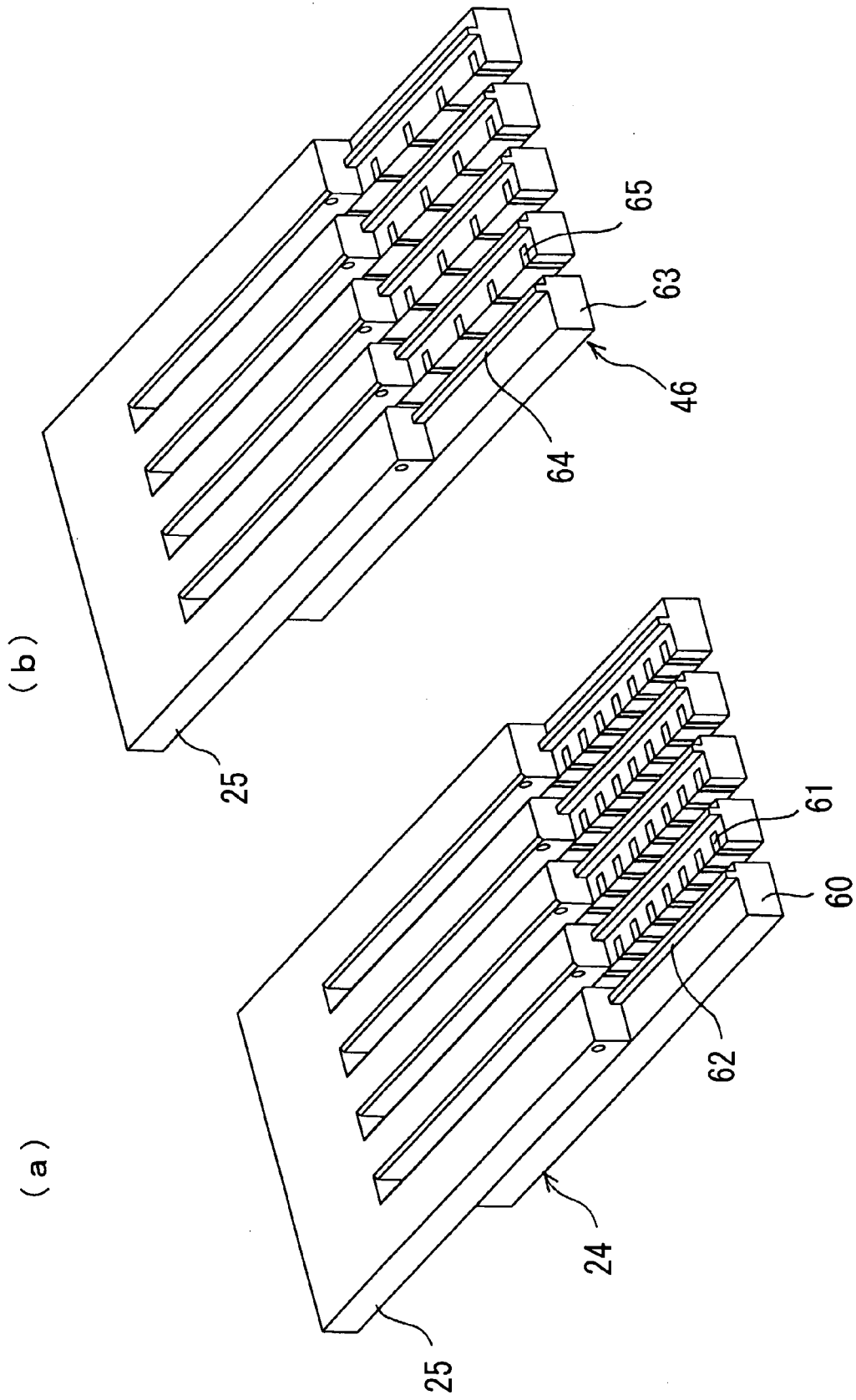
FIG. 5 are perspective views illustrating comb teeth magnets in the embodiments of the invention.

FIG. 5(*b*) is a perspective view illustrating the comb teeth magnet 46 and the comb teeth light-detecting unit 25, which are in the state that they are taken out. The comb teeth magnet 46 has magnets 65, the total number of which is 24, arranged to be brought into contact with the dispensing tips 15 and separated therefrom, so as to apply a magnetic field simultaneously to the insides of the dispensing tips 15, as nozzles, and remove the magnetic field.

The comb teeth magnet 46 has: comb teeth members 63 that are arranged in gaps between adjacent rows of the dispensing tips 15 having a row interval set to a "2" multiple, the number "2" being the natural number of each of the row interval and the column interval of the wells 39, 40, 41 and 42, so as to be movable along the row direction, that extend along the row direction, and that are fitted to have a width permitted to be inserted in any one of gaps between adjacent rows of the dispensing tips 15, the number of the comb teeth members 63 being 4, which is the row number of the dispensing tips 15; and a supporting member 63*a* connected to single-ends of the comb teeth members 63 and extending in the column direction. Each of the comb teeth members 63 is equipped with magnets 65 arranged to have a column interval set to a "2" multiple as the natural number multiple of the column interval of the wells, correspondingly to the positions of the dispensing tips 15 as individual nozzles. The column number of the magnets 61 is 1/"2" as one to the natural number, so as to be 1. That is, the number of the magnets 61 is 6.

In the figure, reference numeral 64 represents a guide rail laid along the longitudinal direction of the comb teeth members 63, that is, the row direction, so as to guide the movement of the above-mentioned comb teeth light-detecting unit 25 arranged on the upper surface of the comb teeth members 63 so as to be movable. The micro plate treating device 30 according to the embodiment has a control unit, not illustrated, for controlling operations of the sucking and discharging mechanism, the moving means, the magnetic force means, and the light-detecting means. The control unit is as described about the micro plate treating device 10 according to the first embodiment.

The following will describe the operation of the micro plate treating device 30 according to the second embodiment, giving, as an example, a treatment for extracting DNA from specimens.

Figure 4:
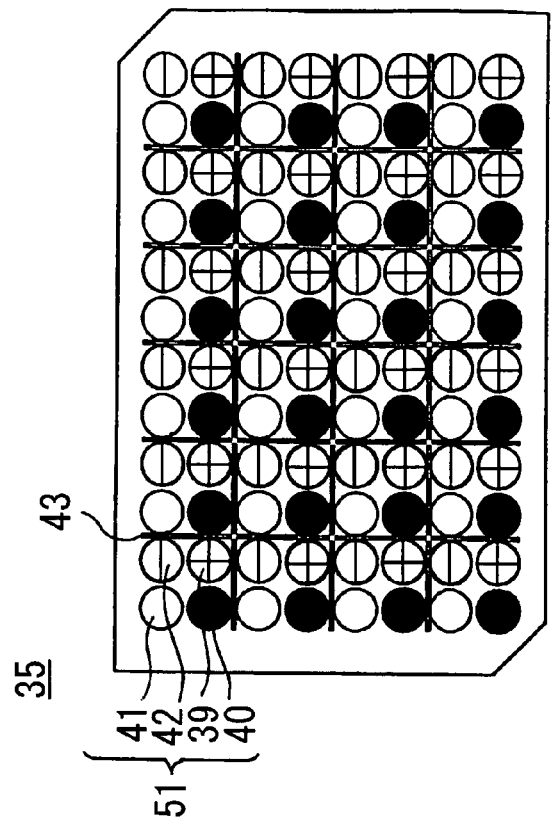
FIG. 4 are explanatory views illustrating partial well matrices and well groups in micro plates in the embodiments of the invention.
Figure 4:
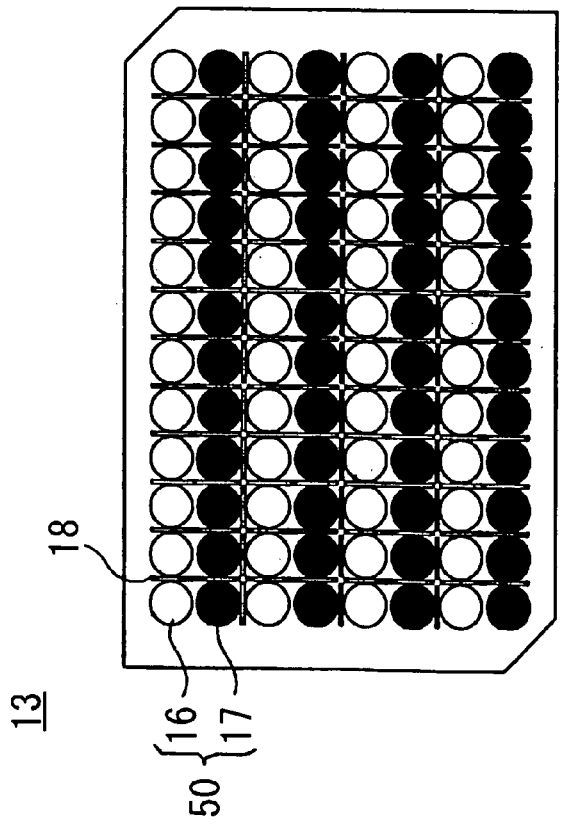

Suspensions of specimens and reagent solutions which are necessary for the treatment are put beforehand in the wells 39, 40, 41 and 42 in each of the micro plates 35, 36, 37 and 38, the specimens and the reagent solutions being those necessary for 4 steps as a whole. For example, as illustrated in FIG. 4(*b*), about the micro plates 35, 36, 37 and 38 each having the wells of 8 rows×12 columns, the number of which is 96, the individual partial well matrices (4 row×6 columns) to which the wells represented by the white circles, the single-lines, the crosses and the black circles belong are used as units to put, beforehand, suspensions capable of capturing the target material (for example, suspensions wherein magnetic particles having function groups on their surfaces are suspended) in the individual wells in the partial well matrix (the wells 41) corresponding to the white circles, put 24 specimens, such as bloods collected from 24 subjects, as treating objects beforehand in the individual wells 42 in the partial well matrix (the wells 42) corresponding to the single-lines, put a reagent necessary for dissolving the specimens in the individual wells 39 in the partial well matrix (the wells 39) corresponding to the crosses, and put a reagent necessary for disassociating the target material from the magnetic particles in the individual wells 40 in the partial well matrix (the wells 40) corresponding to the black circles.

The nozzle heads 31-34 are each moved along a predetermined moving path by the moving means, thereby conducting successive treatment operations. First, the individual dispensing tips 15, the number of which is 24, of each of the nozzle heads 31, 32, 33 and 34 are positioned in such a manner that the tips 15 can be simultaneously inserted into the partial well matrix (the wells 41) to which the wells 41 containing the specimens represented by the white circles belong. In each of the 4 nozzle heads 31, 32, 33 and 34, all the dispensing tips 15, the number of which is 24, are simultaneously inserted into the wells corresponding to the partial well matrix (the wells 41) in each of the micro plates 35,36,37 and 38, so that the suspensions of the magnetic particles are sucked.

Whether or not the suction is attained is based on the following: the light-detecting comb teeth members 66 of the comb teeth light-detecting units 25 fitted to the nozzle heads 31, 32, 33 and 34 are moved in the row direction, whereby the states of the liquids in the individual dispensing tips 15 are measured. Next, the nozzle heads 31, 32, 33 and 34 are each moved upwards to pull out the dispensing tips 15 from the partial well matrix (the wells 41). The tips 15 are then moved along the row direction by the column interval. In this way, the 24 dispensing tips 15 are positioned in such a manner that the tips 15 can be simultaneously inserted into the partial well matrix (the wells 42) to which the wells 42 represented by the single-lines in each of the micro plates 35, 36, 37 and 38 belong. Then, all the 24 dispensing tips 15 are simultaneously inserted into all the wells 42 corresponding to the partial well matrix (the wells 42), so as to discharge the suspensions of the magnetic particles into the individual specimen solutions.

The dispensing tips 15 are pulled out from the partial well matrix (the wells 42). The tips 15 are then moved along the column direction by the row interval. In this way, the dispensing tips 15, the number of which is 24 per nozzle head, are positioned in such a manner that the tips 15 can be simultaneously inserted into the partial well matrix (the wells 39) to which the wells 39 represented by the crosses belong. Then, all the 24 dispensing tips 15 in each of the 4 nozzle heads 31, 32, 33 and 34 are simultaneously inserted into the wells 39 corresponding to the partial well matrix (the wells 39), so as to repeat a suction and a discharge. In this way, the specimens and the magnetic-particle-mixed suspensions are discharged thereinto, so as to cause them together with, for example, the reagent in which the specimens can be dissolved to react with each other. In this way, DNA or the like is extracted from the specimens, and then adsorbed to the magnetic particles.

Such a suction and a discharge by means of the dispensing tips 15 are repeated. Thereafter, the comb teeth members 63 of the comb teeth magnets 46 fitted to the nozzle heads 31, 32, 33 and 34 are moved to be inserted into gaps between the rows of the dispensing tips 15, so as to cause the individual magnets 65 to approach the individual dispensing tips 15. A magnetic field is then applied to the insides of the individual tips 15 from the external. In this state, such a suction and a discharge are repeated to cause the magnetic particles to be adsorbed onto inner walls of the dispensing tips 15. In this way, the magnetic particles are separated.

Next, in the state that the magnetic particles are caused to be adsorbed, the dispensing tips 15 are pulled out from the individual wells in the partial well matrix. The nozzle heads 31, 32, 33 and 34 are then moved in the row direction by the column interval so as to move all the dispensing tips 15 in each of the nozzle heads 31, 32, 33 and 34 in such a manner that the tips 15 can be inserted into the partial well matrix (the wells 40) to which the wells 40 represented by the black circles in each of the micro plates 35, 36, 37 and 38 belong. Then, all the dispensing tips 15 are simultaneously inserted into all the wells 40 in the partial well matrix (the wells 40). The comb teeth magnets 46 are then moved to separate the individual magnets 65 from the dispensing tips 15, thereby removing the magnetic field. A suction and a discharge are repeated, together with the disassociating liquid held in the wells 40 in the partial well matrix (the wells 40), thereby attaining re-suspension. A magnetic field is again applied thereto, so as to cause only the magnetic particles to be adsorbed onto the inner walls of the dispensing tips 15, whereby the magnetic particles are removed. In this way, the target nucleic acid, such as DNA, can be extracted.

According to the treatment according to the embodiment, the 4 nozzle heads having a total nozzle number equal to the number of the wells in any one of the micro plates are used to treat the 4 micro plates simultaneously; therefore, the moving distance between the micro plates is short although the treating speed thereof is equal to the treating speed of a nozzle head having nozzles the number of which is equal to the number of wells in any one of the micro plates. Thus, the treating speed as a whole increases. Moreover, the number of steps can be increased by making the treating period or the number of micro plates unchanged.

In the above-mentioned treatment, the moving path of the nozzle heads 31, 32, 33 and 34 is a path along which the individual dispensing tips 15 arranged therein pass through the wells 41, 42, 39 and 40 in the order thereof. For this reason, treatment operations in the 4 micro plates can be simultaneously conducted in parallel, in the unit of each of the 4 partial well matrices, although there are used the nozzle heads wherein the number of their dispensing tips is 96, which is equal to the number of the wells in each of the micro plates.

Figure 7:
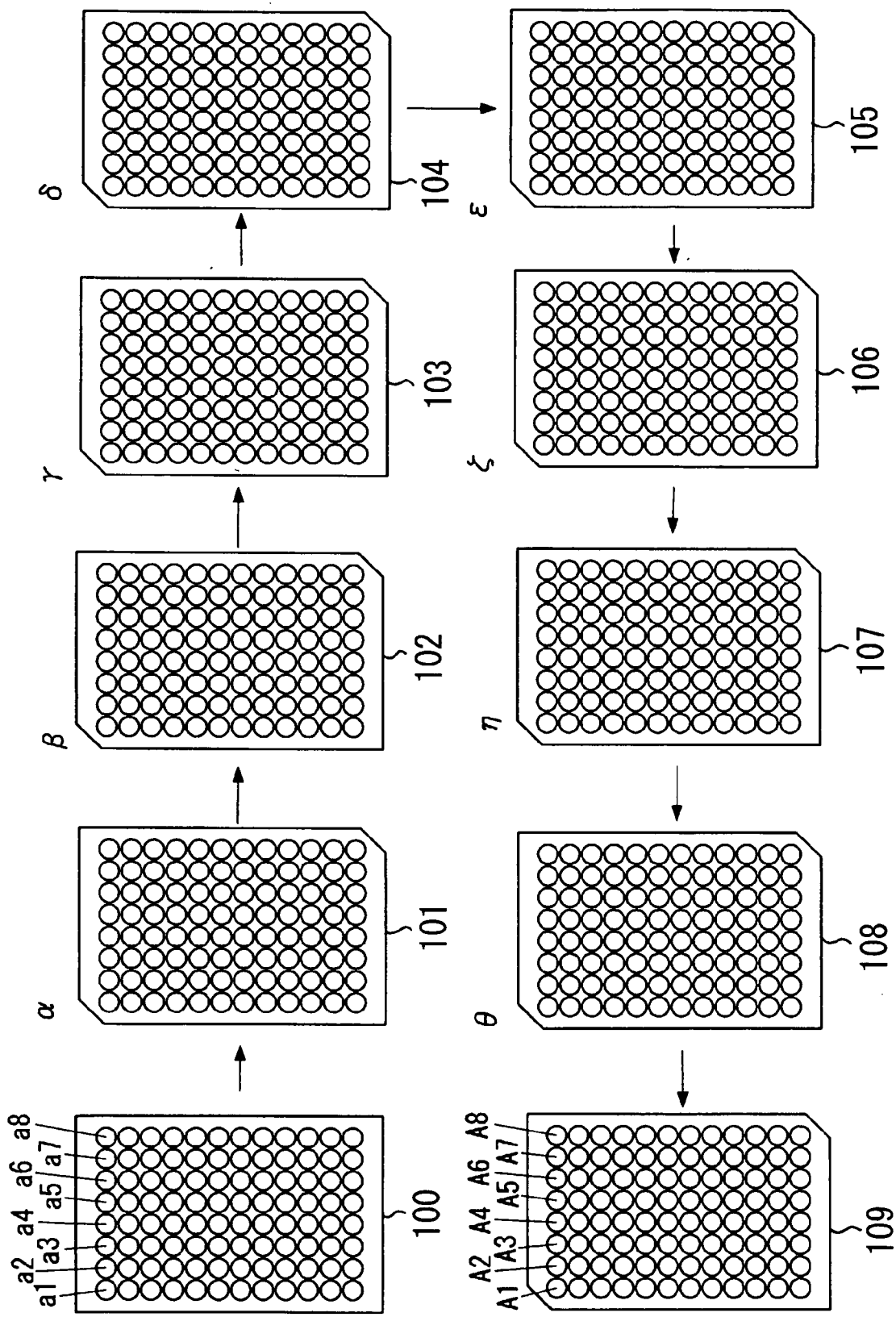
FIG. 7 is a schematic view illustrating a treating situation that micro plates in the prior art are used.
Figure 8:
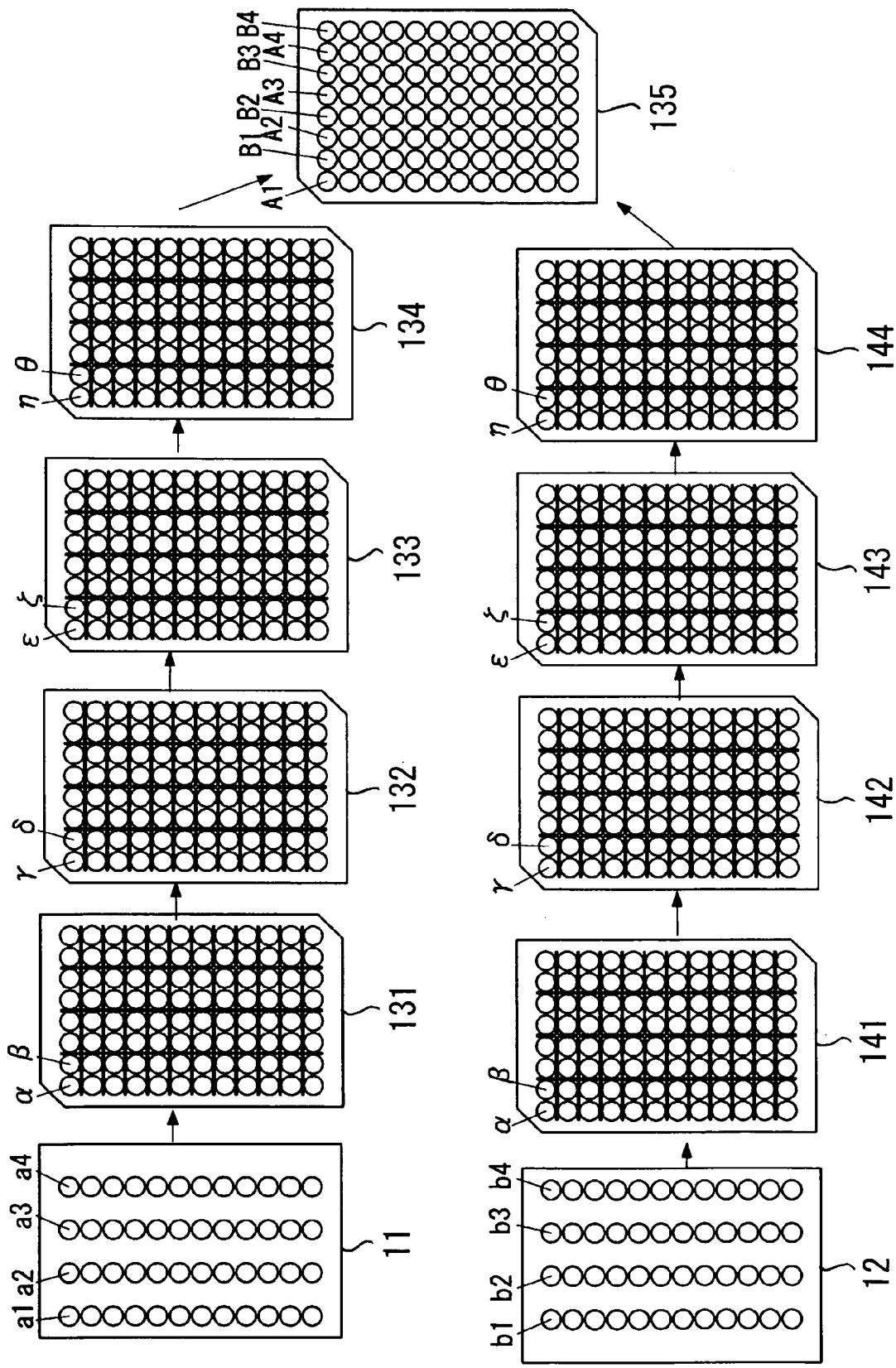
FIG. 8 is a schematic view illustrating a treating situation that micro plates according to the first embodiment of the invention are used.
Figure 9:
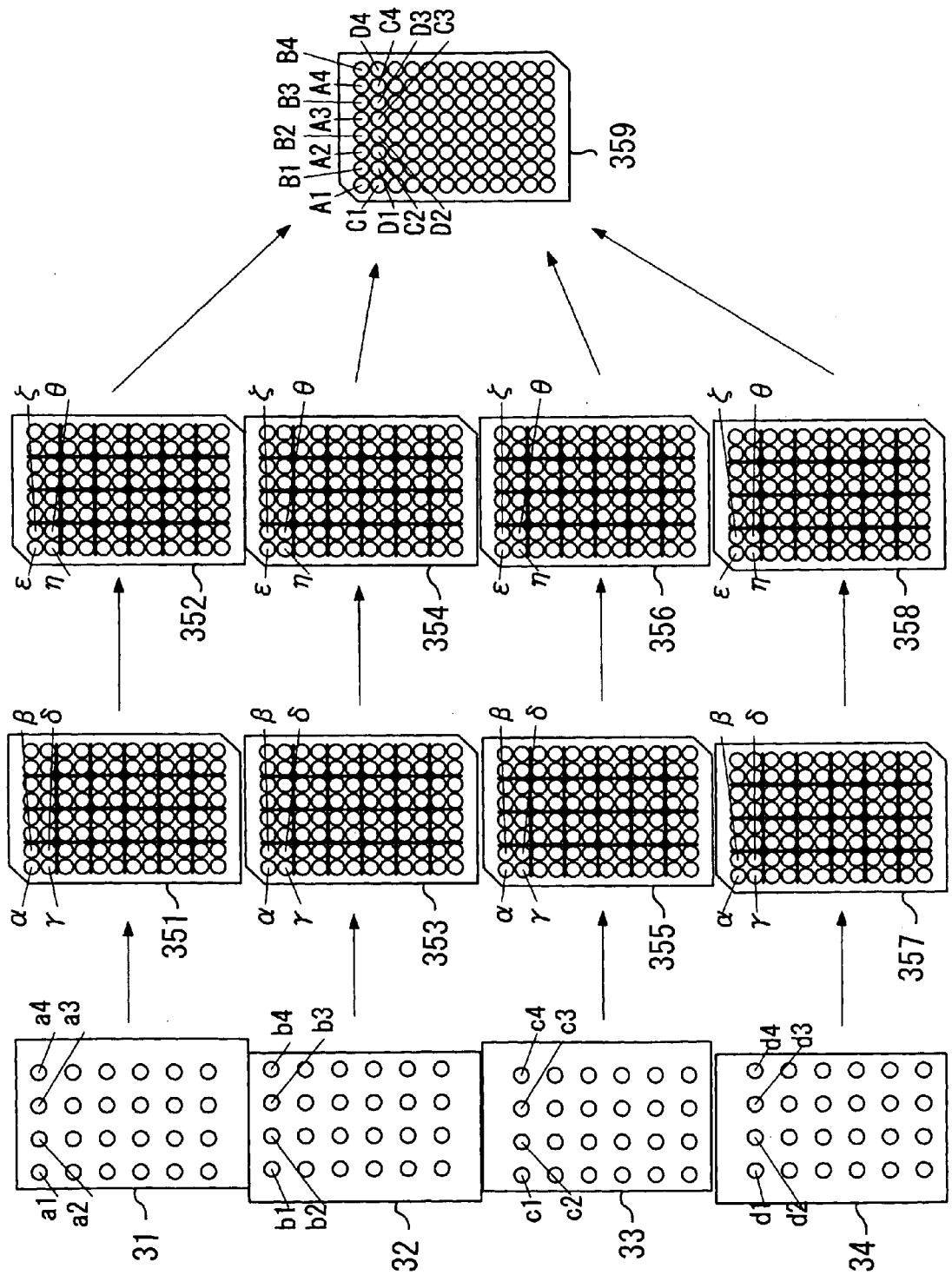
FIG. 9 is a schematic view illustrating a treating situation that micro plates according to the second embodiment of the invention are used.

FIGS. 7 to 9 each schematically illustrate a situation that micro plates, and a nozzle head or nozzle heads are used in the case of conducting treatment using a magnetic particle suspension ($\alpha$), a specimen suspension ($\beta$), and 6 reagents ($\gamma, \ldots \theta$).

FIG. 7 illustrates a treatment using a device in the prior art. In this case, 8 micro plates 101 to 108, which each have 96 wells of 8 rows×12 columns, are prepared. A nozzle head 100 is used wherein 96 nozzles (dispensing tips a1 to a8) having the same configuration as the wells are arranged. The micro plates 101 to 108 each contain any one of the magnetic particle suspension, the specimen suspension, and the 6 reagent solutions in accordance with the order of the treatment operations. The treatment is conducted by repeating a suction and a discharge by moving the magnetic particles successively to the individual micro plates by use of the nozzle head 100. In order to complete the treatment, it is necessary to move the nozzle head 100 along the 8 micro plates 101 to 108. Final products therefrom are held in a micro plate 109.

FIG. 8 illustrates a treatment using the micro plate treating device 10 according to the first embodiment. In this case also, 8 micro plates 131 to 134 and 141 to 144, which each have 96 wells of 8 rows×12 columns, are prepared. The two nozzle heads 11 and 12 are used, wherein 48 nozzles (dispensing tips a1 to a4, and b1 to b4) of 4 rows×12 columns are arranged. Accordingly, the total number of the nozzles is 96. Contents held in the individual micro plates 131 to 134 are equivalent with those held in the individual micro plates 141 to 144. In each of the micro plates, two selected from the same magnetic particle suspension, specimen suspension and six reagent solution as above in accordance with the order of steps for the treatment are held in the two partial well matrices, respectively, the partial well matrices each having a configuration corresponding to the configuration of the nozzle head 11 or 12. The nozzle heads 11 and 12 are used to move the magnetic particles successively to the individual micro plates, and in the each of the micro plates, the nozzle head 11 or 12 is moved by the row interval of the two partial well matrices, thereby repeating a suction and a discharge so as to conduct the treatment. The treatment operations are simultaneously completed in the two nozzle heads. In this case, it is sufficient that the individual nozzle heads 11 and 12 are simultaneously moved by a distance corresponding to 4 out of the micro plates; thus, the moving distance is shorter and the treatment can be more speedily attained than in the prior art. The final products are held in a micro plate 140; the final products include products obtained by effect of the nozzle head 11 and those obtained by effect of the nozzle head 12. Well matrices for the two are classified into elements "A" and "B".

FIG. 9 illustrates an example of a treatment using the micro plate treating device 30 according to the second embodiment. In this case also, 8 micro plates 351 to 358, which each have 96 wells of 8 rows×12 columns, are used as a whole. The 4 nozzle heads 31, 32, 33 and 34 are used, wherein 24 nozzles (a1 to a4, b1 to b4 and c1 to c4) of 4 rows×6 columns are arranged. Accordingly, the total number of the nozzles is 96. Contents held in the micro plates 351, 353, 355 and 357 are equivalent with those held in the micro plates 352, 354, 356 and 358, respectively. In each of the micro plates, 4 selected from the same magnetic particle suspension, specimen suspension and 6 reagent solutions as above in accordance with the order of steps for the treatment are held in the 4 partial well matrices, respectively, the partial well matrices having configurations corresponding to the configurations of the nozzle heads 31, 32, 33 and 34. The nozzle heads 31, 32, 33 and 34 are used to move the magnetic particles successively to the individual micro plates, and in the each of the micro plates, one of the nozzles is moved by the row interval and the column interval of the 4 partial well matrices, thereby repeating a suction and a discharge so as to conduct the treatment. In this way, the treatment operations are simultaneously conducted in the 4 nozzle heads, thereby completing the treatment.

In this case, it is sufficient that the individual nozzle heads 31, 32, 33 and 34 are simultaneously moved between the two micro plates 351 and 352, the micro plates 353 and 354, the micro plates 355 and 366, and micro plates 357 and 358, respectively; thus, the moving distance is even far shorter and the treatment can be even more speedily attained. The final products are put in a micro plate 359 in the unit of each of the 4 partial well matrices, which are composed of individual elements "A", "B", "C" and "D", by use of the individual nozzle heads.

The individual embodiments described above are embodiments described specifically in order to cause the invention to be more satisfactorily understood. Thus, the invention is not limited to the embodiments. Accordingly, the invention can be modified as far as the subject matter of the invention is not varied. For example, as the nozzles, only dispensing tips fitted to nozzles have been described; however, the nozzles are not limited thereto. Nozzles to which no dispensing tips are fitted may be used. As the sucking and discharging mechanism, only a cylinder has been described; however, the following mechanism may be used: a mechanism using bellows-type dispensing tips and causing the tips to be deformed, the tips having a container which can put liquid and gas onto the inside surrounded by wall faces that partially have a deformable wall face which can be deformed into a predetermined form without changing the entire inner surface area of the wall faces substantially, and a mouth, connected to the container, through which a liquid sucked or discharged by expansion and contraction of the inside by the deformation of the deformable wall face can be caused to flow in and flow out.

The above-mentioned description has referred to a case where only one out of two nozzle heads is used to conduct treatment in the micro plate treating device 10 according to the first embodiment; however, it is needless to say that the invention is not limited to the case. Furthermore, the description has referred to only a case where micro plates having 96 wells are used; however, the invention is not limited to the case of the micro plates. Thus, the invention can cope with micro plates the various number of wells. As the example of the treatment, treatment for extracting nucleic acid has been briefly described; however, the treatment is not limited to this treatment. The words "rows" and "columns" are words for convenience, and may be used in the state that they are exchanged for each other.

Industrial Applicability

The micro plate treating device and the micro plate treating method according to the invention are concerned with all fields, example of which are fields of industry, agricultures such as foods, agricultural production and fishery processing, pharmacy, medicals, wherein as hygiene, insurance, diseases and inheritance and others are handled, chemistry, biology, and other fields in which treatments of various solutions are required. The invention is particularly useful for cases of carrying out a series of treatment operations of many objects in a predetermined order by use of many reagents or materials in parallel.

Description of Reference Numerals 10, 30 micro plate treating devise
    11, 12, 31, 32, 33, 34, 100 nozzle heads
    13, 14, 35, 36, 37, 38, 131-134, 135, 141-144, and 351-359 micro plates
    15 dispensing tip
    16, 17, 39, 40, 41, 42 wells
    24, 46 comb teeth magnets (magnetic force means)
    25 comb teeth light-detecting unit (light-detecting means)
    50, 51 well groups

The invention claimed is:

1. A micro plate treating device, comprising a micro plate having wells arranged in a first matrix form, the first matrix form comprising a first plurality of rows and a first plurality of columns, at least one pair of adjacent rows in the first plurality of rows defining a first row interval therebetween, at least one pair of adjacent columns in the first plurality of columns defining a first column interval therebetween, one or two or more nozzle heads each having nozzles arranged in a second matrix form, the second matrix form comprising a second plurality of rows and a second plurality of columns, at least one pair of adjacent rows in the second plurality of rows defining a second row interval therebetween, at least one pair of adjacent columns in the second plurality of columns defining a second column interval therebetween, and moving means capable of effecting relative movement between the micro plate and the nozzle heads, wherein tips of all the nozzles arranged in each of the nozzle heads are configured to be permitted to be simultaneously inserted into some of the wells in the micro plate, at least one of the second row interval and the second column interval is set to a natural number multiple of the first row interval or the first column interval, the natural number being two or more, and at least one of the number of rows in the first plurality of rows and the number of columns in the first plurality of columns is one to the natural number of the number of rows in the second plurality of rows or the number of columns in the second plurality of columns, and wherein the micro plate treating device further comprises two or more magnets positioned between said nozzle heads and said micro plate and fitted to be relatively moved either within the second row interval and along a row of nozzles in the at least one pair of adjacent rows in the second plurality of rows, or within the second column interval and along a column of nozzles in the at least one pair of adjacent columns in the second plurality of columns, whereby the magnets can approach respective nozzles in either the row of nozzles or the column of nozzles and separated therefrom in such a manner that the magnets are brought into contact with, or are positioned at respective distances from, the respective nozzles so that a magnetic field is simultaneously applied to the insides of the respective nozzles.

2. The micro plate treating device according to claim 1, which further comprises a control unit, wherein the control unit is programmed to cause the moving means to effect the relative movement between the nozzle head and the micro plate, thereby causing the tips of all the nozzles fitted to the nozzle head to be positioned in such a manner that the tips can be simultaneously inserted into the respective wells belonging to a first portion of the first matrix form in the micro plate, inserting the tips of the nozzles simultaneously into the respective wells belonging to the first portion so that a treatment operation is conducted, pulling out the tips; and then to cause the moving means to effect the relative movement between the nozzle head and the micro plate, thereby causing the tips of all the nozzles to be positioned in such a manner that the tips can be simultaneously inserted into the respective wells belonging to a second portion of the first matrix form in the micro plate.

3. The micro plate treating device according to claim 2, wherein the respective wells belonging to the first portion contain solutions or suspensions necessary for individual steps of the treatment operation in accordance with the order of the steps.

4. The micro plate treating device according to claim 2, wherein the control unit is programmed to cause the nozzle head to be successively moved so as to position the tips of the nozzles in the state that the tips can be inserted into all the wells in the micro plate, into which the tips of the same nozzles fitted to the nozzle head can be inserted.

5. The micro plate treating device according to claim 1, wherein partitions for partitioning the well groups, in the micro plate, are built on the upper surface of the micro plate so as to be projected therefrom.

6. The micro plate treating device according to claim 1, wherein the number of the nozzle heads and the number of the micro plate are each at least a natural number.

7. The micro plate treating device according to claim 1, further comprising: a comb teeth member to which the magnets are fitted, which can be moved relatively to the nozzle heads, and which extends along the row of nozzles or the column of nozzles, the comb teeth member having a width that permits the comb teeth member to be inserted in the second row interval or the second column interval, and a supporting member connected to the comb teeth member.

8. The micro plate treating device according to claim 1, wherein each of the nozzle heads further comprises light-detecting means for detecting the state of liquid in the nozzles.

9. The micro plate treating device according to claim 8, wherein: the light-detecting means comprises a light-detecting comb teeth member that can be moved relatively to the nozzle heads, the light-detecting comb teeth member having a width that permits the light-detecting comb teeth member to be inserted in the second row interval or the second column interval, a supporting member connected to the light-detecting comb teeth member; and at least one light-detecting unit set up to each of the light-detecting comb teeth member.

\* \* \* \* \*